US007488834B2

(12) United States Patent
Dötz et al.

(10) Patent No.: US 7,488,834 B2
(45) Date of Patent: Feb. 10, 2009

(54) ORGANIC SEMICONDUCTORS

(75) Inventors: Florian Dötz, Heidelberg (DE); Howard E. Katz, Owings Mills, MD (US); Elsa Reichmanis, Westfield, NJ (US); Subramanian Vaidyanathan, New Providence, NJ (US); Ingolf Hennig, Neulussheim (DE)

(73) Assignees: Alcatel-Lucent USA Inc., Murray Hill, NJ (US); BASF Societas Europea, Ludwigshafan (DE)

( * ) Notice: Subject to any disclaimer, the term of this patent is extended or adjusted under 35 U.S.C. 154(b) by 24 days.

(21) Appl. No.: 11/241,642

(22) Filed: Sep. 30, 2005

(65) Prior Publication Data

US 2007/0078267 A1    Apr. 5, 2007

(51) Int. Cl.
C07D 333/10 (2006.01)
H01L 31/20 (2006.01)

(52) U.S. Cl. .......................................... 549/80; 257/40
(58) Field of Classification Search ................... 549/80; 257/40

See application file for complete search history.

(56) References Cited

U.S. PATENT DOCUMENTS

| | | | |
|---|---|---|---|
| 6,265,243 B1 | 7/2001 | Katz et al. | 438/99 |
| 6,403,397 B1 | 6/2002 | Katz | 438/99 |
| 6,551,717 B2 | 4/2003 | Katz et al. | 428/447 |
| 6,803,262 B2 | 10/2004 | Wu et al. | 438/149 |
| 6,855,951 B2 | 2/2005 | Ong et al. | 257/40 |
| 6,890,868 B2 | 5/2005 | Wu et al. | 438/781 |
| 6,897,284 B2 | 5/2005 | Liu et al. | 528/373 |
| 2003/0227014 A1 | 12/2003 | Murti et al. | 257/40 |
| 2005/0040394 A1 | 2/2005 | Wu et al. | 257/40 |
| 2005/0184274 A1 | 8/2005 | Heeney et al. | 252/299.01 |
| 2005/0205861 A1 | 9/2005 | Bao et al. | 257/40 |

FOREIGN PATENT DOCUMENTS

| | | |
|---|---|---|
| DE | 103 40 643 A1 | 4/2005 |
| WO | WO 02/45184 A1 | 6/2002 |
| WO | WO 03/052841 A1 | 6/2003 |
| WO | WO 2004/057688 A1 | 7/2004 |
| WO | WO2006/024012 A1 | 3/2006 |

OTHER PUBLICATIONS

Apperloo, et al, "Solvent effects on the pi-dimerization of cation radicals of conjugated oligomers," Synthetic Materials 101(1999), pp. 373-374.*

Yokooji, et al, "Synthesis of 5,5'-diarylated-2,2'-bithiophenes via palladium-catalyzed arylation reactions," Tetrahedron 60(2004), pp. 6757-6763.*

CAPLUS Accession No. 1999:459430, abstract of Apperloo et al, Synethetic Materials (1999).*

Yokooji, et al, "Synthesis of 5,5'-diarylated-2,2'bithiophenes via palladium-catalyzed arylation reactions," Tetrahedron 60(2004), pp. 6757-6763.*

Li et al., "Field-Effect Transistors Based on Thiophene Hexamer Analogues with Diminished Electron Donor Strength", Chem. Mater., vol. 11, pp. 458-465 (1999).

Veres et al., "Low-$k$ Insulators as the Choice of Dielectrics in Organic Field-Effect Transistors", Advanced Functional Materials, vol. 13, No. 3, pp. 199-204 (Mar. 2003).

Mushrush et al., "Easily Processable Phenylene—Thiophene-Based Organic Field-Effect Transistors and Solution-Fabricated Nonvolatile Transistor Memory Elements", J. Am. Chem. Soc., vol. 125, pp. 9414-9423 (2003).

Chabinyc et al., "Short channel effects in regioregular poly(thiophene) thin film transistors", Journal of Applied Physics, vol. 96, No. 4, pp. 2063-2070 (Aug. 15, 2004).

Arias et al., "All jet-printed polymer thin-film transistor active-matrix backplanes", Applied Physics Letters, vol. 85, No. 15., pp. 3304-3306 (Oct. 11, 2004).

Ong et al., "High-Performance Semiconducting Polythiophenes for Organic Thin-Film Transistors", J. Am. Chem. Soc., vol. 126, pp. 3378-3379 (2004), plus supplementary materials (6 pgs).

Chabinyc et al., "Lamination Method for the Study of Interfaces in Polymeric Thin Film Transistors", J. Am. Chem. Soc., vol. 126, pp. 13928-13929 (2004).

Zhao et al., "Microscopic Studies on Liquid Crystal Poly (3,3'''-dialkylquaterthiophene) Semiconductor" Macromolecules, vol. 37, pp. 8307-8312 (2004).

Salleo et al., "Intrinsic hole mobility and trapping in a regioregular poly(thiophene)", Physical Review B, vol. 70, pp. 115311-1 to 115311-10 (2004).

Ong et al., "Polythiophene-based field-effect transistors with enhanced air stability", Synthetic Metals, vol. 142, pp. 49-52 (2004).

Wu et al., "High-Performance Organic Thin-Film Transistors with Solution-Printed Gold Contacts", Advanced Materials, vol. 17, No. 2, pp. 184-187 (Jan. 31, 2005).

Li et al., "Novel Peripherally Substituted Indolo[3,2-$b$]carbazoles for High-Mobility Organic Thin-Film Transistors", Advanced Materials, vol. 17, No. 7, pp. 849-853 (Apr. 4, 2005).

Ong et al., "Structurally Ordered Polythiophene Nanoparticles for High-Performance Organic Thin-Film Transistors", Advanced Materials, vol. 17, pp. 1141-1144 (2005).

Wu et al., "Poly(3,3'''-dialkylterthiophene)s: Room-Temperature, Solution-Processed, High-Mobility Semiconductors for Organic Thin-Film Transistors", Chem. Mater., vol. 17, pp. 221-223 (2005), plus supporting information (2 pgs).

(Continued)

Primary Examiner—Rei-Tsang Shiao
Assistant Examiner—Janet L Coppins

(57) ABSTRACT

A molecule including a chain-like core region having two ends and having at least three conjugated aromatic rings; and including at the two ends, branched groups $R^1$ and $R^2$ respectively, each including a $C_5$- to $C_{20}$-alkyl group. A semiconducting composition including the molecule.

19 Claims, 6 Drawing Sheets

OTHER PUBLICATIONS

Locklin et al., "Organic Thin Film Transistors Based on Cyclohexyl-Substituted Organic Semiconductors", *Chem. Mater.*, vol. 17, pp. 3366-3374 (2005).

Wu et al., "Indolo[3,2-b]carbazole-Based Thin-Film Transistors with High Mobility and Stability", *J. Am. Chem. Soc.*, vol. 127, pp. 614-618 (2005).

Li et al., "Facile Synthesis of Silver Nanoparticles Useful for Fabrication of High-Conductivity Elements for Printed Electronics", *J. Am. Soc.*, vol. 127, pp. 3266-3267 (2005), plus supporting information (6 pgs).

Dötz et al., "Liquid Phase Fabrication of Active Devices Including Organic Semiconductors", Unpublished U.S. Appl. No. 11/240,222, filed Sep. 30, 2005 (77 pgs).

Dötz et al., "Organic Compositions", Unpublished U.S. Appl. No. 11/240,733, filed Sep. 30, 2005 (49 pgs).

Facchetti et al., "Synthesis and Characterization of Diperfluorooctyl-Substituted Phenylene-Thiophene Oligomers . . . ", *Chem. Mater.*, vol. 16, pp. 4715-4727 (2004)

\* cited by examiner

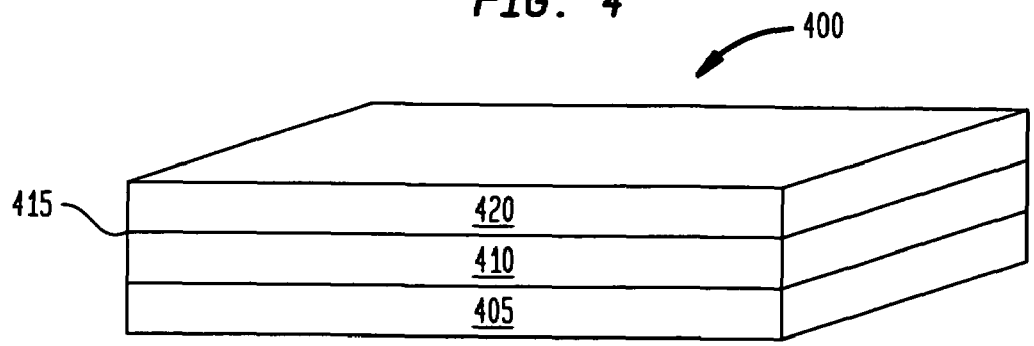
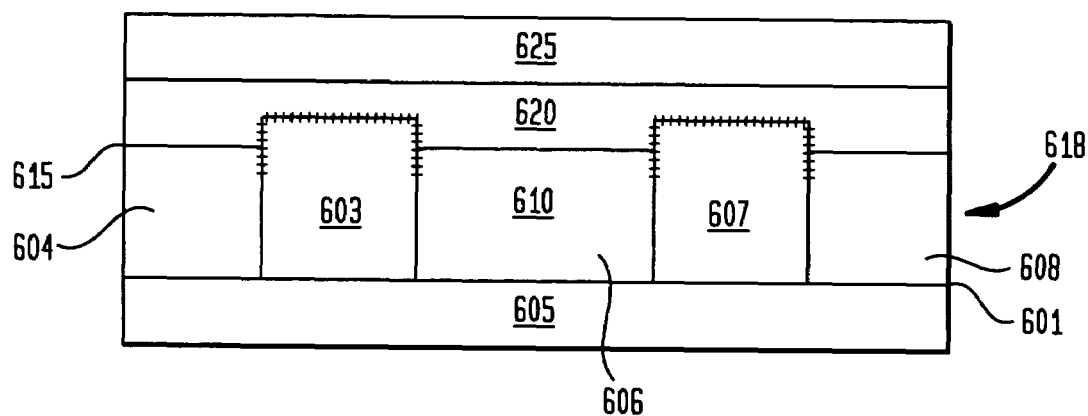
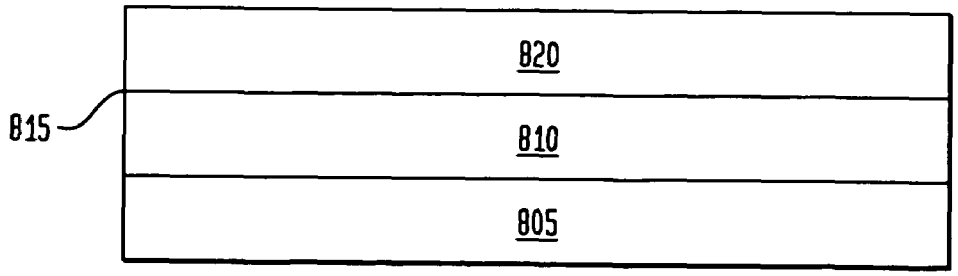

ORGANIC SEMICONDUCTORS

FIELD OF THE INVENTION

The present invention relates to the field of organic semiconductors and devices incorporating them.

BACKGROUND OF THE INVENTION

Organic electronics is an emerging field of technology which aims to realize low-cost and environmentally-friendly fabrication of electronic devices. Organic field effect transistors ("FETs") are potential alternatives to amorphous silicon transistors, and may be useful for instance in relatively low-speed devices with utility as pixel drivers of active matrix displays and in radio frequency identification devices. Potential advantages to making organic FETs instead of silicon-based or other inorganic-based transistors include the possibilities of large-area and low-temperature processing, which may for example help enable fabrication of electronics on flexible plastic substrates.

Films of inorganic semiconductors are often brittle and inflexible such that their fabrication into devices may be carried out on rigid silicon wafers yielding devices that themselves are inflexible. Films formed from organic semiconductors, in contrast, are often bendable and flexible such that their fabrication into devices may potentially be carried out by continuous processes using, for example, a flexible web support body. The resulting devices themselves often also have the potential to be bendable and flexible, opening up possible end use applications that are often impracticable for inorganic semiconductor-based devices.

Continuous processes for the formation of devices incorporating organic semiconductors may include steps for printing the organic semiconductors onto a substrate. In order to carry out such printing steps in a continuous process, the organic semiconductor composition may need to be both compatible with a given printing process and compatible with the substrate on which the semiconductor composition is to be printed. For example, the organic semiconductor composition may need to have a viscosity or other physical properties that enable the organic semiconductor composition to be deposited by the continuous printing process onto a substrate and to adhere as intended to the substrate.

Accordingly, there is a need for new organic semiconductor compositions that may, for example, facilitate the printing of an organic semiconductor onto a substrate.

SUMMARY OF THE INVENTION

In one example of an implementation, a molecule is provided, including a chain-like core region having two ends and having at least three conjugated aromatic rings; and including at the two ends, branched groups $R^1$ and $R^2$ respectively, each including a $C_5$- to $C_{20}$-alkyl group.

In another implementation, a molecule is provided, having the following formula:

wherein $R^1$ and $R^2$ each include branched $C_5$- to $C_{20}$-alkyl groups.

Semiconducting compositions including the molecules are also provided.

A more complete understanding of the present invention, as well as other features and advantages of the invention, will be apparent from the following detailed description and the accompanying drawings.

BRIEF DESCRIPTION OF THE DRAWINGS

FIG. 4 shows a cross sectional perspective view of an example of a laminate including a support body having bonded thereon an organic semiconductor composition body and a dielectric composition body;

FIG. 6 shows a cross-sectional side view of another example of a laminate including a support body having bonded thereon an organic semiconductor composition body and a dielectric composition body;

FIG. 8 shows a cross-sectional side view of an example of a laminate including a support body having bonded thereon a dielectric composition body and an organic semiconductor composition body;

DETAILED DESCRIPTION

Figure 1:
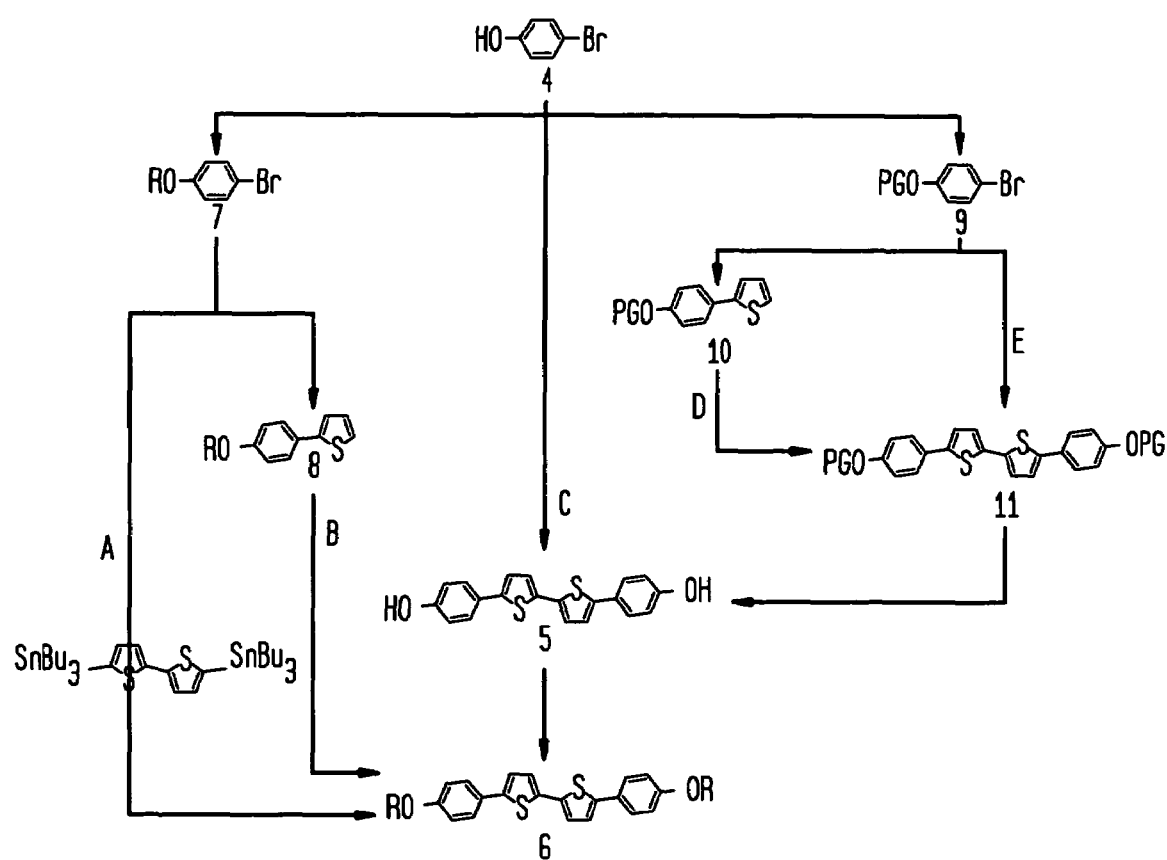
FIG. 1 shows synthesis scheme 1 routes A, B, C, and D for organic semiconductors as designated in Table 1.

Examples will now be described more fully with reference to the accompanying drawings, in which several examples are shown. Various additional forms may be used, and this disclosure should not be construed as being limited to the examples set forth herein.

The present invention provides an organic semiconductor molecule, including a chain-like core region having two ends and having at least three conjugated aromatic rings; and including at the two ends, branched groups $R^1$ and $R^2$ respectively, each including a $C_5$-to $C_{20}$-alkyl group. "Branched" means that a linear carbon skeleton is supplemented by a side-substituent other than hydrogen. As an example, groups $R^1$ and $R^2$ may be carbon-branched. As an example, each of the conjugated aromatic rings may be selected from the group consisting of a thiophene ring and a benzene ring. In another example, other types of conjugated aromatic rings, which may be substituted or unsubstituted and which may include heteroatoms, may be included or substituted for thiophene and benzene rings. As a further example, any thiophene rings in the core region may be 2,5-linked and any benzene rings in the core region may be 1,4-linked. In another example, each of the two ends may be selected from the group consisting of a 2-linked thiophene ring, and a 1-linked benzene ring. In an example of an implementation, each of $R^1$ and $R^2$ may be either 5-linked to a thiophene ring or 4-linked to a benzene ring. As another example, each of $R^1$ and $R^2$ may include, optionally ether at an end of or within a $C_5$- to $C_{20}$-alkyl group, an ether moiety. In a further implementation example, $R^1$ and $R^2$ may each be linked by an ether bond to the core region. The core region may, as an example, have between three and seven conjugated aromatic rings. In an additional implementation, each of $R^1$ and $R^2$ may include a branched $C_5$- to $C_{16}$-alkyl group. As an example, $R^1$ and $R^2$ may be acyclic.

The branched groups $R^1$ and $R^2$ (also referred to as "alkyl side chains") may be saturated or include unsaturation, and may be unsubstituted or may include substituents. The alkyl side chains may include one or more non-aromatic cycloalkyl groups. As an example, a cyclohexyl, cyclopentyl, or cyclobutyl group may be included. The cycloalkyl groups may be saturated or contain some unsaturation. In an example, the organic semiconductor molecule may include a plurality of 2,5-linked thiophene rings and 1,4-linked benzene rings, which is substituted with one, two, or more alkyl side chains of 5 to 20 carbon atoms in length. By "2,5-linked" is meant that any linkages between a thiophene ring and another ring may be made at the 2 or 5 positions of the thiophene moiety, the sulfur atom being at the 1 position. By "1,4-linked" is meant that any linkages between a benzene ring and another ring may be made at mutually -para positions of the benzene moiety. In a further example, the organic semiconductor molecule may include two 2,5-linked thiophene rings and two 1,4-linked benzene rings, the thiophene rings being interposed between the benzene rings, the molecule being substituted at each of the two terminal 4 positions of the benzene rings with an alkyl chain of 5 to 20 carbon atoms in length. In another example, the organic semiconductor molecule may include a 2,5-linked thiophene tetramer, pentamer or other-mer, substituted at each of the two 5-positions of the terminal thiophene rings with an alkyl chain of 5 to 20 carbon atoms in length.

In one example, the organic semiconductor molecule includes one or more of the following class of molecules:

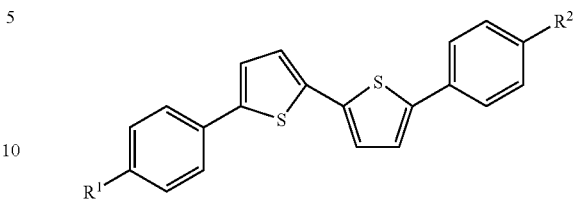

Formula 1 wherein $R^1$ and $R^2$ each include branched $C_5$- to $C_{20}$-alkyl groups; in each case optionally including, either at an end of or within the branched $C_5$- to $C_{20}$-alkyl groups, an ether moiety, an aldehyde moiety, an alkyl amide moiety, and optionally including substitution by hydroxy, a protective group such as tetrahydropyrane or diphenyl tert butyl silane, or a crosslinkable moiety such as -1-vinyl-allyl esters. The structure of $R^1$ may be different than the structure of $R^2$, or the structure of $R^1$ may be the same as the structure of $R^2$.

In one example, substituents for $R^1$ and $R^2$ may be selected to have an electronegativity of about 3.5 or less. Substituents having electronegativity greater than about 3.5 may have an electron withdrawing effect on the aromatic rings sufficient to unduly reduce p-type charge carrier mobility in the organic semiconductor composition. $R^1$ and $R^2$ may include some substitution by —Cl, —Br, and —I. Excessive halogenation and substitution by —F may induce n-type charge carrier mobility in the organic semiconductor composition. Substituents for $R^1$ and $R^2$ may also include other functional groups, for example, nitro, amino, sulfonyl and carbonyl, provided that such functional groups are sufficiently distanced from the aromatic core region so as not to adversely affect charge carrier mobility.

In case of any molecules above having stereoisomeric centers including as examples, molecules among those within the above Formula (1), both the racemic mixtures and the optically active stereoisomers are contemplated. It is to be understood that all of the above classes of semiconductor molecules may be in monomeric form or may be linked, while still satisfying the above-defined structural requirements, into polymeric forms. Polymeric semiconductors tend to have lower charge carrier mobility than do small organic molecules. The alkyl side chains in relatively small molecules may aid in crystal packing, leading to better alignment and higher charge carrier mobility. The side chains may also serve as a protective barrier to degradation by oxygen and water. Small organic molecules may have higher charge carrier mobility, on/off ratios, and chemical stability. However, polymers may more easily form elongated films from liquid phase deposition. Here, "small organic molecules" means molecules having a well defined molecular weight, for example, a molecular weight of less than about 1,000 grams per Mole.

In a further example, the organic semiconductor molecule may include one or more of the organic semiconductors that are shown in Table 1.

TABLE 1

| Short Name | Molecular Structure | Example Synthesis Routes  S = synthetic procedure; P = purification; and Y = yield. | Formulation and processing (solubility, viscosity of formulation, deposition on substrate, film quality) |
|---|---|---|---|
| 6-O-PTTP-O-6 | Molecular Weight = 518.79  Exact Mass = 518  Molecular Formula = C32H38O2S2  Molecular Composition = C 74.09% H 7.38% O 6.17% S 12.36%  5,5'-bis(4-hexyloxy phenyl)-2,2'-bithiophene | S: route A, FIG. 2  P: repeated crystallisation  Y: 25%  heavy loss during P | solubility in THF about 600 ppm, lowest value by far. Differential scanning calorimetry ("DSC"); melting point = 243° C., smaller transitions at 65, 148, 176, 255, 261° C. (doastereomers or LC) |
| 5(4Me)-O-PTTP-O-5(4Me) | Molecular Weight = 518.79  Exact Mass = 518  Molecular Formula = C32H38O2S2  Molecular Composition = C 74.09% H 7.38% O 6.17% S 12.36%  5,5'-bis(4-(4-methylpentyloxy)phenyl)-2,2'-bithiophene | S: route A, FIG. 2  P: repeated crystallization  Y: 31%  heavy loss during P | solubility in THF about 5400 ppm. DSC: mp = 250° C., smaller transition around 173° C. (could be LC) |
| 8(3,7Me)-O-PTTP-O-8(3,7Me) | Molecular Weight = 631.00  Exact Mass = 630  Molecular Formula = C40H54O2S2  Molecular Composition = C 76.14% H 8.63% O 5.07% S 10.16%  5,5'-bis(4-(3,7-dimethyloctyloxyphenyl)-2,2'-bithiophene | S: route A, FIG. 2  P: repeated crystallization  Y: 15%  heavy loss during P | solubility in THF about 12,000 ppm DCS: mp = 192° C., smaller transition at 143° C. (diastereomer or LC) |

TABLE 1-continued

Figure 2:
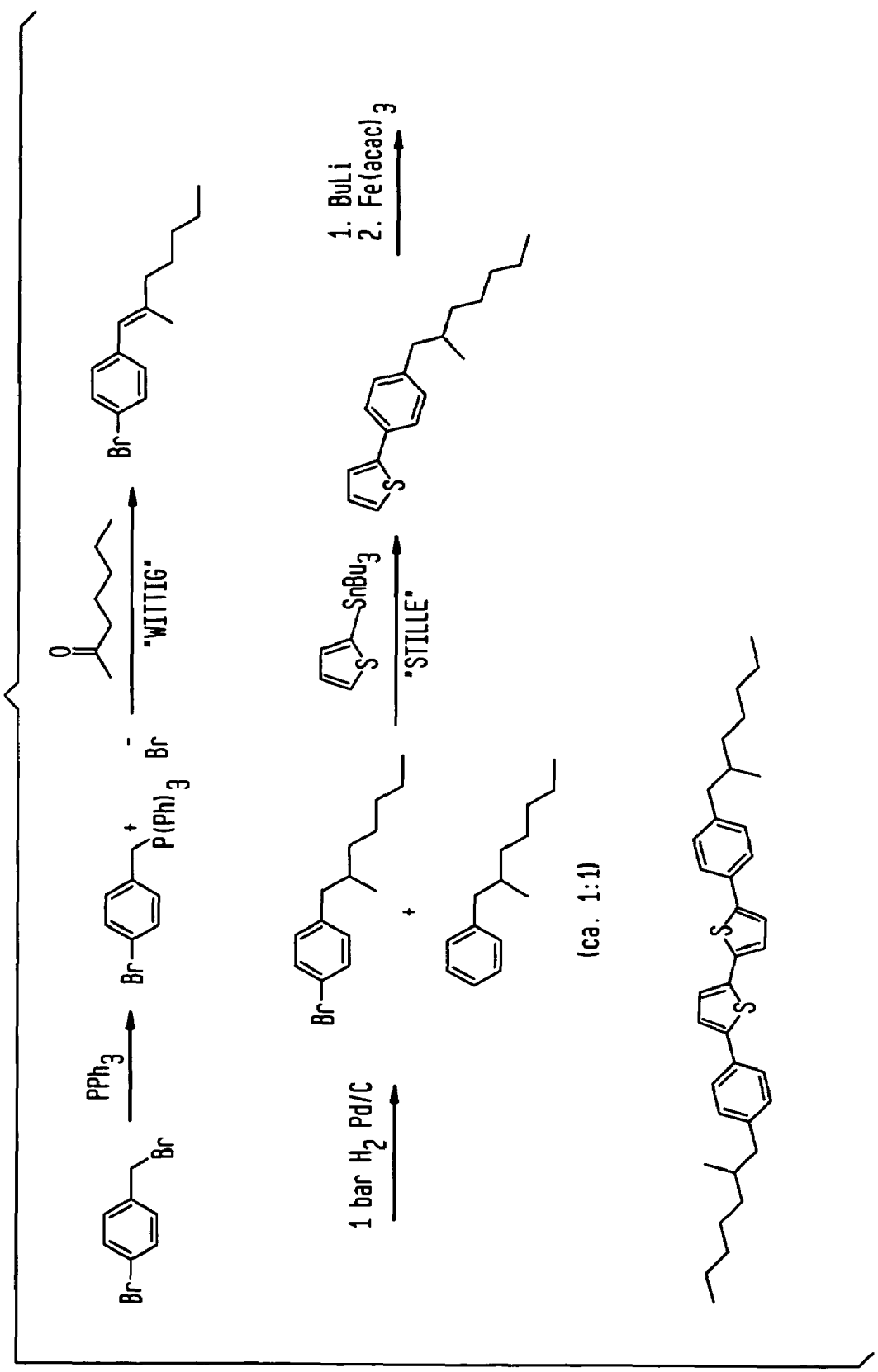
FIG. 2 shows synthesis scheme 2 for organic semiconductors as designated in Table 1.

| Short Name | Molecular Structure | Example Synthesis Routes<br>S = synthetic procedure;<br>P = purification; and<br>Y = yield. | Formulation and processing (solubility, viscosity of formulation, deposition on substrate, film quality) |
|---|---|---|---|
| 8(3S,7Me)-O-PTP-P-8(3S,7Me) | Molecular Weight = 631.00<br>Exact Mass = 630<br>Molecular Formula = C40H54O2S2<br>Molecular Composition = C 76.14% H 8.63% O 5.07% S 10.16%<br>5,5'-bis(4-(3S,7-dimethylcotyloxy)phenyl)-2,2'-bithiophene | S: route B, FIG. 2<br>P: extraction<br>Y: 63%, optically pure | |
| 4(2Et)-O-PTP-O-4(2Et) | Molecular Weight = 518.79<br>Exact Mass = 518<br>Molecular Formula = C32H38O2S2<br>Molecular Composition = C 74.09% H 7.38% O 6.17% S 12.36%<br>5,5'-bis(4-(2-ethylbutyloxy)phenyl)-2,2'-bithiophene | S: route B, FIG. 2<br>P: precipitation, extraction<br>Y: 37% | solubility in THF about 4,900 ppm |

TABLE 1-continued

| Short Name | Molecular Structure | Example Synthesis Routes S = synthetic procedure; P = purification; and Y = yield. | Formulation and processing (solubility, viscosity of formulation, deposition on substrate, film quality) |
|---|---|---|---|
| 6(2Me)-O-PTTP-O-6(2Me) | 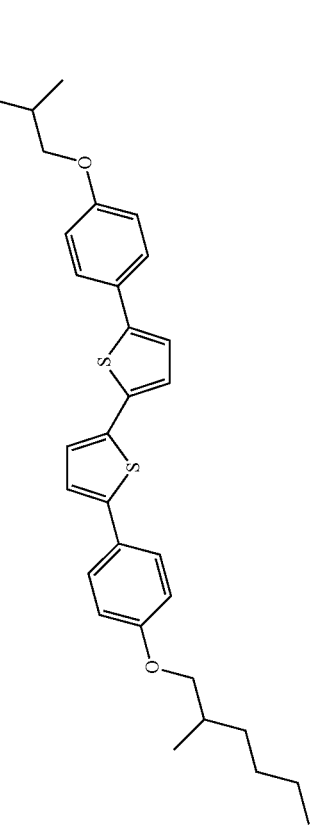<br>Molecular Weight = 546.84<br>Exact Mass = 546<br>Molecular Formula = C34H42O2S2<br>Molecular Composition = C 74.68% H 7.74% O 5.85% S 11.73%<br>5,5'-bis(4-(2-methylhexyloxy)phenyl)-2,2'-bithiophene | S: route B, FIG. 2<br>P: extraction<br>Y: 47% | sufficiently soluble in THF (about 61,000 ppm)<br>DSC: mp = 197° C. |
| 6(2Et)-O-PTTP-O-6(2Et) | 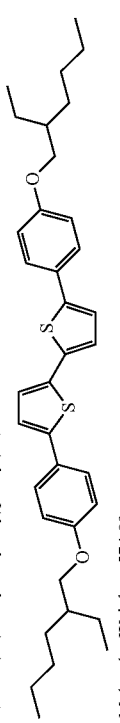<br>Molecular Weight = 574.89<br>Exact Mass = 574<br>Molecular Formula = C36H46O2S2<br>Molecular Composition = C 75.21% H 8.07% O 5.57% S 11.15%<br>5,5'-bis(4-(2-ethylhexyloxy)phenyl)-2,2'-bithiophene | S: route A, FIG. 2<br>P: chromatography<br>Y: 5%<br>heavy loss during P<br>S: route B<br>P: precipitation<br>Y: 29 and 26% | sufficiently soluble in THF (about 70,000 ppm) and o-xylene (about 25,000 ppm); viscosity η = 22 mPa·s at c = 500 ppm, cyclohexanol/THFA/THF = 86:9:5)<br>DSC: mp = 148° C., smaller transition between 75° C. and 105° C. (only in heating cycle) |

TABLE 1-continued

| Short Name | Molecular Structure | Example Synthesis Routes<br>S = synthetic procedure;<br>P = purification; and<br>Y = yield. | Formulation and processing<br>(solubility, viscosity of formulation, deposition on substrate, film quality) |
|---|---|---|---|
| 6(1Me)-O-PTTP-O-6(1Me); also referred to as 1-MH-PTTP | 5,5'bis(4-(1-methylhexyloxy)phenyl)-2,2'-bithiophene<br><br>Molecular Weight = 546.84<br>Exact Mass = 546<br>Molecular Formula = C34H42O2S2<br>Molecular Composition = C 74.68% H 7.74% O 5.85% S 11.73% | S: route D, FIG. 2<br>P: filtration (SiO$_2$),<br>Y: 19<br>S: route B, FIG. 2<br>P: extraction<br>Y: 52, 37, 51 and 44%<br>S: route B, FIG. 2<br>P: 2 x precipitation.<br>from toluene with methanol<br>Y: 39% | well soluble in THF (about 89,000 ppm); o-xylene 54,000 ppm;<br>THF/cyclohexanol 2:8 (viscosity 9 mPas)<br>4,000 ppm;<br>2-Ethylhexanol: about 800 ppm<br>DSC: mp = 143° C., smaller transition at 118° C., 129° C., and 132° C. |
| 6(1Et)-O-PTTP-O-6(1Et) | 5,5'-Bis-[4-(1-ethyl-hexyloxy)-phenyl]-[2,2']bithiophenyl<br><br>Molecular Weight = 574.89<br>Exact Mass = 574<br>Molecular Formula = C36H46O2S2<br>Molecular Composition = C 75.21% H 8.07% O 5.57% S 11.15% | S: route B, FIG. 2<br>P: extraction<br>Y: 55% | Well soluble in THF (about 330,000 ppm)<br>DSC: mp = 97-102° C., (broad transition) |

TABLE 1-continued

| Short Name | Molecular Structure | Example Synthesis Routes S = synthetic procedure; P = purification; and Y = yield. | Formulation and processing (solubility, viscosity of formulation, deposition on substrate, film quality) |
|---|---|---|---|
| 6(6TBDPSO)-O-PTTP-O-6(6TBDPSO) | 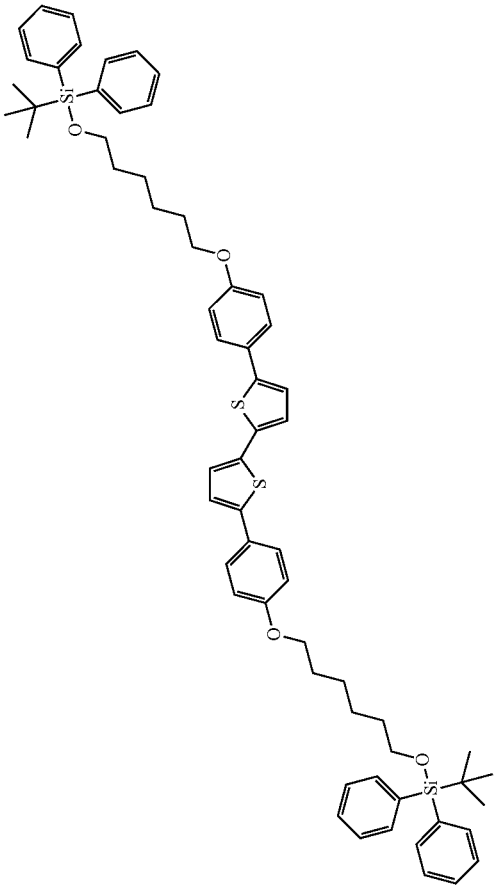<br>Molecular Weight = 1027.60<br>Exact Mass = 1026<br>Molecular Formula = C64H74O4S2Si2<br>Molecular Composition = C 74.81% H 7.26% O 6.23% S 6.24% Si 5.47%<br>5,5'-Bis-{4-[6-(tert-butyl-diphenyl-silanyloxy)-hexyloxy]-phenyl}-[2,2']bithiophenyl | S: route B, FIG. 2<br>P: extraction<br>Y: 74%<br>Precursor for terminal OH-alkyl PTTP | Well soluble in THF (about 310,000 ppm); |

TABLE 1-continued

| Short Name | Molecular Structure | Example Synthesis Routes<br>S = synthetic procedure;<br>P = purification; and<br>Y = yield. | Formulation and processing (solubility, viscosity of formulation, deposition on substrate, film quality) |
| --- | --- | --- | --- |
| 3(3THPO,2Me)-O-PTTP-O-3(THPO,2Me) | Molecular Weight = 662.91<br>Exact Mass = 662<br>Molecular Formula = C36H46O6S2<br>Molecular Composition = C 68.85% H 6.99% O 14.48% S 9.67%<br>5,5'-Bis-[4-(2-methyl-propoxy-tetrahydro-pyran)-phenoxy]-[2,2']bithiophenyl | S: route B, FIG. 2<br>P: extraction<br>Y: 48% | Well soluble in THF (about 75,000 ppm) |
| 3(3OH,2Me)-O-PTTP-O-3(3OH,2Me) | Molecular Weight = 494.68<br>Exact Mass = 494<br>Molecular Formula = C28H30O4S2<br>Molecular Composition = C 67.99% H 6.11% O 12.94% S 12.96%<br>3-(4-{5'-[4-(3-Hydroxy-2-methyl-propoxy)-phenyl]-[2,2']bithiophenyl-5-yl}-phenoxy)-2-methyl-propan-1-ol | S: route B, FIG. 2<br>P: extraction<br>Y: 59% | Low solubility in THF (600 ppm) |

TABLE 1-continued

| Short Name | Molecular Structure | Example Synthesis Routes<br>S = synthetic procedure;<br>P = purification; and<br>Y = yield. | Formulation and processing (solubility, viscosity of formulation, deposition on substrate, film quality) |
|---|---|---|---|
| 5[5(1,4diene)O₂C]-O-PTTP-O-5[5(1,4dieneO₂C] | Molecular Weight = 710.96<br>Exact Mass = 710<br>Molecular Formula = C42H46O6S2<br>Molecular Composition = C 70.96% H 6.52% O 13.60% S 9.02%<br>6-[4-(5'-[5-(1-Vinyl-allyloxycarbonyl)-pentyloxy]-phenyl]-[2,2']bithiophenyl-5-yl)-phenoxy]-hexanoic acid 1-vinyl-allyl ester | S: route B, FIG. 2<br>P: precipitation<br>Y: 64% | well soluble in THF (131,000 ppm) |
| 3O2PTTP2O3 | 5,5'-Bis(4-(propxy ethyl)phenyl)-2,2'-bithiophene | S: route F, reported below. | Solubility like 6PTTP6 |

The organic semiconductor molecules described above including those shown in Table 1 can be synthesized by procedures that are now detailed. In one example where the organic semiconductor molecule includes 5,5'-Bis-[4-(1-methyl-hexyloxy)-phenyl]-[2,2']bithiophene ("1-MH-PTTP"), the 1-MH-PTTP may be synthesized, as an example, by the following three steps.

Step 1. Synthesis of 1-Bromo-4-(1-methyl-hexyloxy)-benzene

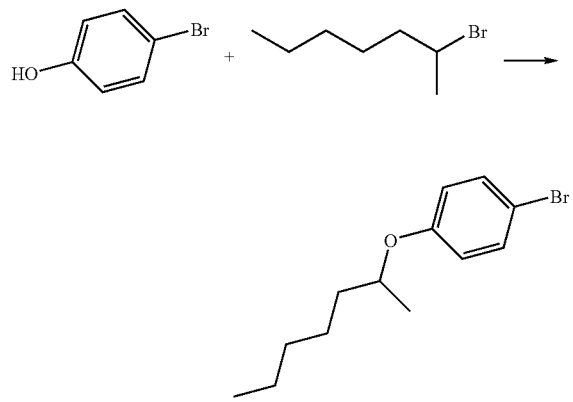

p-Bromophenol (295.52 grams ("g"), 1500.00 millimole) is dissolved in anhydrous dimethyl formamide ("DMF") (500 milliliters ("mL") in a 2000 milliliter ("mL") 3-necked flask equipped with mechanical stirrer and condenser, under an argon atmosphere. To this solution, (1-methyl) hexylbromide (322.38 grams, 1800.00 millimoles), sodium iodide (33.57 g, 225.00 mmol) and anhydrous potassium carbonate (621.95 g, 4500.00 mmol) are added. The resulting suspension is heated to 100° C. and stirred at that temperature for 72 hours. After cooling to room temperature, water (1000 mL) and n-hexane (300 mL) are added. The aqueous layer is separated and extracted with n-hexane (3×100 mL). The combined organic layers are washed with diluted sodium chloride solution (2×100 mL) and dried (MgSO$_4$). The solvent is removed by rotary evaporation under reduced pressure and the residue is filtered using a SiO$_2$ layer (10×10 cm) and n-hexane as eluent. After removal of solvent by rotary evaporation and in vacuo a colorless liquid (245.54 g, 60%) is obtained.

Step 2. Synthesis of 2-[4-(1-Methyl-hexyloxy)-phenyl]-thiophene

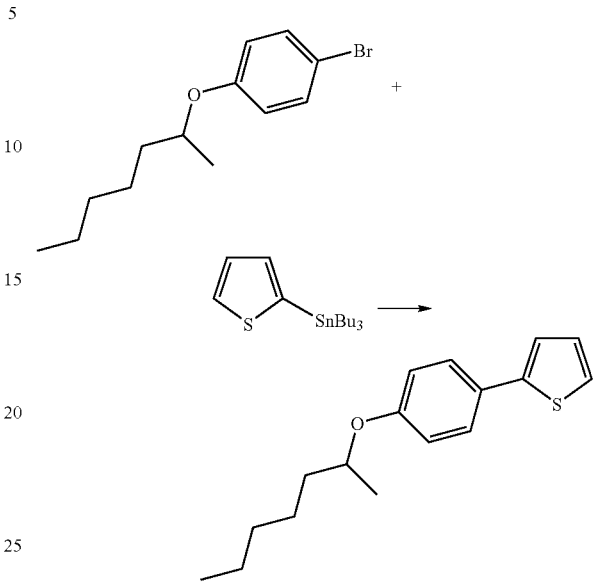

Tetrakistriphenylphosphinpalladium(0), (20.45 g, 17.70 mmol) is suspended in anhydrous DMF (400 mL) in a 2000 mL 3-necked flask with magnetic stirrer and condenser under an argon atmosphere. To this, 1-bromo-4-(1-methyl-hexyloxy)-benzene (240.00 g, 884.96 mmol) and tri-n-butylstannylthiophene (330.24 g, 884.96 mmol) are added. The resulting solution is stirred at 100° C. for 68 hours. After cooling to room temperature the mixture is poured into water (2000 mL) and divided into two portions of the same volume. Extraction with n-hexane (3×300 mL) results in two layers and an emulsion between those two layers. The organic layers are separated, combined, washed with diluted sodium chloride solution (2×400 mL) and dried (MgSO$_4$). After removal of solvent by rotary evaporation most of the byproducts are removed by distillation (p=10$^{-3}$ millibar, maximum temperature $T_{max}$=130° C.). The residue is subjected to filtration using a layer of SiO$_2$ (30×10 cm) and n-hexane as eluent. After removal of solvent, a yellowish oil (107.88 g, about 44%) with sufficient purity for synthetic purposes is obtained.

Step 3. Synthesis of 5,5'-Bis-[4-(1-methyl-hexyloxy)-phenyl]-[2,2']bithiophene (1-MH-PTTP)

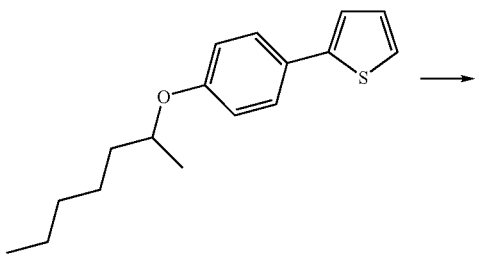

-continued

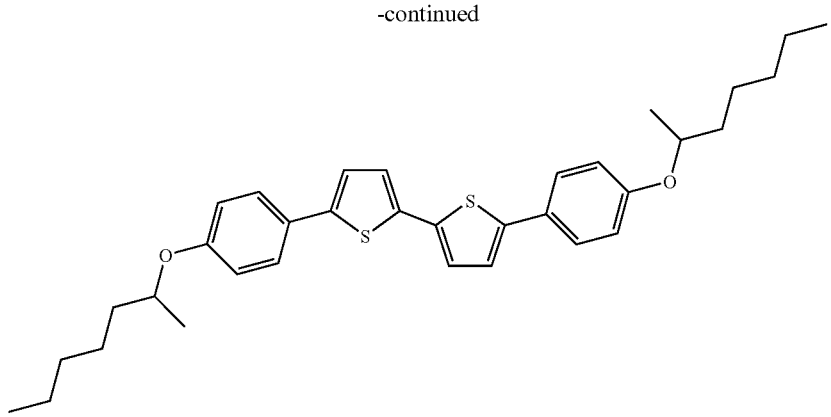

In a 2000 mL 3-necked flask equipped with mechanical stirrer, condenser and dropping funnel, 2-[4-(1-Methyl-hexyloxy)-phenyl]-thiophene (26.00 g, 94.74 mmol) is dissolved in anhydrous tetrahydrofuran ("THF") (250 mL) under an argon atmosphere. Then n-BuLi (2.5M in hexanes, 41.68 mL, 104.22 mmol) is added at −70° C. within about 15 min by a syringe. The solution is stirred for 1 h at that temperature. A solution of tris-(2,4-pentadionato)-iron(III) (33.48 g, 94.74 mmol) in anhydrous THF (400 mL) is transferred to the dropping funnel under an argon atmosphere and added to the lithiated 2-[4-(1-Methyl-hexyloxy)-phenyl]-thiophene at −70° C. within about 45 min. The mixture is then allowed to warm to room temperature and heated to reflux for 1 h. After cooling the solvents are removed by rotary evaporation under reduced pressure. The residue is transferred to an extraction thimble and extracted with MeOH (900 mL) overnight using a Soxhlet-apparatus to remove most of the iron compounds. The deep orange colored extract is discarded and the thimble is dried in a continuous stream of nitrogen. The extraction is continued to completeness using n-hexane (900 mL). From the extract the product precipitates upon cooling as a pale orange solid. After separation of the solid by filtration using a folded filter and drying, it is extracted a second time using methanol (900 mL) for about 2 h until the extract is pale yellow. The methanolic solution is discarded and the thimble is dried as described above. Complete extraction using n-hexane (900 mL) and cooling of the resulting solution yields the pure product as a bright yellow solid (10.78 g, 42%).

Figure 3:
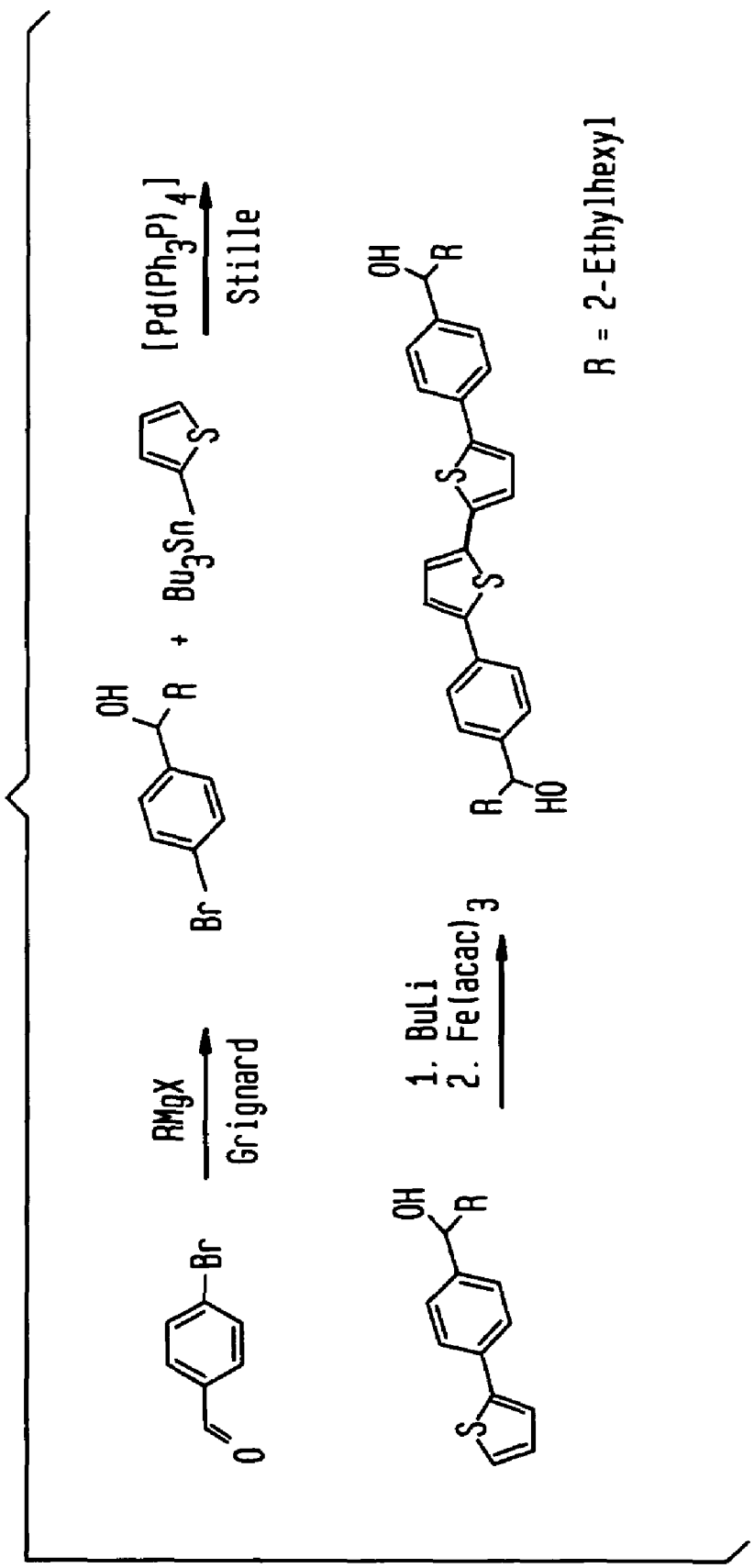
FIG. 3 shows synthesis scheme 3 for organic semiconductors as designated in Table 1.

FIG. 1 shows synthesis scheme 1 routes A, B, C, and D as designated above in Table 1. R designates an organic moiety. PG designates a protecting group. FIG. 2 shows synthesis scheme 2 as designated above in Table 1. Ph is "phenyl". The abbreviation "acac" is acetylacetonate. FIG. 3 shows synthesis scheme 3 as designated above in Table 1. "Mushrush" designates: Mushrush, M., Facchetti, A., Lefenfeld, M., Katz, H. E., and Marks T. J., "Easily processable phenylene-thiophene-based organic field-effect transistors and solution-fabricated nonvolatile transistor memory elements", *J Am. Chem. Soc.*, vol. 125, pp. 9414-9423 (2003), which is hereby incorporated herein by reference in its entirety.

The molecule 3O2PTTP2O3 was synthesized according to route F shown below, by adapting the synthesis procedure for 6PTTP6 (Mushrush), starting with (2-(4-bromophenyl)-ethyl) propyl ether instead of 4-hexyl bromobenzene. A mixture of 2-(4-bromophenyl)-ethanol (25 mmol, 5 g), 1-iodopropane (58 mmol, 10 g) and sodium hydride (27 mmol, 660 mg) was refluxed overnight in 200 ml THF. This refluxed composition was then cooled to room temperature and the organic layer was poured into water (200 mL). The organics were extracted with ethyl ether (3×200 mL), and the combined organics were then concentrated under vacuum to remove the solvents. Column chromatography of the residue (20:1 hexane/ethyl acetate eluent) and removal of solvents yielded the product (2-(4-bromophenyl)-ethyl) propyl ether in 33% yield. The composition was isolated by precipitation in methanol, and purified by repeated recrystallization in toluene.

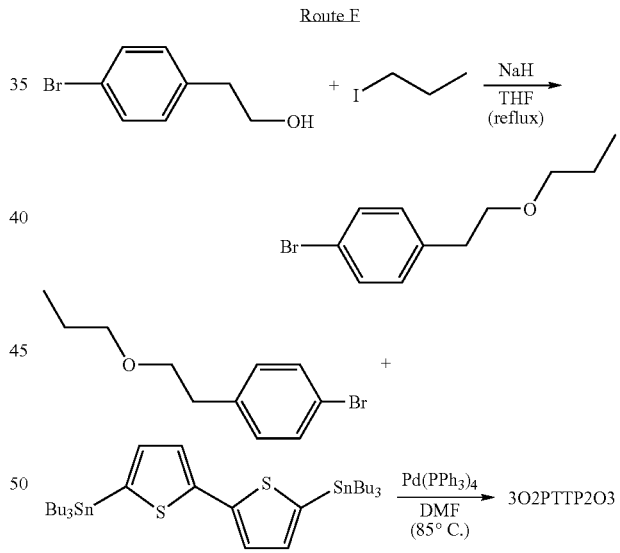

In one example, the organic semiconductor molecules may be utilized in the fabrication of a field effect transistor ("FET"). FIG. 4 shows a cross-sectional perspective view of an example of an implementation of a laminate 400 having a support body 405 having bonded thereon an organic semiconductor composition body 410. The organic semiconductor composition body 410 forms an interface 415 with a dielectric composition body 420 bonded to the body 410. The organic semiconductor composition body 410 is interposed between the support body 405 and the dielectric composition body 420. The laminate 400 may for example be fabricated by first providing the organic semiconductor composition body 410 on the support body 405, and then providing the dielectric composition body 420 to form the interface 415 with the organic semiconductor composition body 410. Further information on fabrication of active devices including organic semiconductor compositions is disclosed in co-owned U.S. patent application Ser. No. 11/240,222, filed concurrently herewith by Florian Dötz, Ingolf Hennig, Jimmy Granstrom, Howard Katz, Elsa Reichmanis, Frauke Richter, and Subramanian Vaidyanathan and entitled "LIQUID PHASE FABRICATION OF ACTIVE DEVICES INCLUDING ORGANIC SEMICONDUCTORS", the entirety of which hereby is incorporated herein by reference.

The term "body" is defined as a solid formed of a designated composition such as an organic semiconductor composition or a dielectric composition. Residual liquid medium from the formation of such bodies, and moisture, for example, may be present. The body may take the form of, for example, a wafer, layer, sheet, or elongated web. An "elongated web" is a sheet having an elongated dimension that is substantially greater than a transverse dimension. An "elongated web" may, for example, be suitable for reel-to-reel continuous processing of a high surface area having a plurality of solid bodies on the elongated web. Any of such forms of solid bodies may be monolithic or multilaminar. For example, a layer may have multiple sub-layers; and an elongated web may have multiple elongated sub webs. A "body" may have a non-uniform thickness and other non-uniform dimensions, and does not have to be completely continuous. A "body" may include one or more bodies of the same material or different materials, which may or may not interpenetrate each other, and which bodies together are referred to as the "body". There is no particular limitation on the thickness or other dimensions of a body, although bodies desirably have dimensions that are optimized for their intended function. The term "laminate" is defined as two or more bodies that are bonded together.

The term "organic" broadly means that the designated composition includes molecules, oligomers, polymers, macromolecules, or other chemical or biological species (collectively "species"), in all cases having a carbon chain that is susceptible to heat-induced structural change, particularly degradation. The carbon chain may constitute a structural skeleton for such species, or merely a partial skeleton or peripheral moiety. An organic composition may include inorganic moieties, species, and elements.

In one example, a selected organic semiconductor composition is soluble in a moderately polar or polarizeable solvent including an aromatic ring and/or having a dipole moment within a range of between about 1 debye and about 3 debye. In another example, such a moderately polar or polarizeable solvent is substantially devoid of free hydroxyl moieties. In a further example, a selected organic semiconductor composition is soluble in a solvent such as methylene chloride, chlorobenzene, toluene, xylene, chloroform, tetrahydrofuran, cyclohexanol, and mixtures. In examples where the organic semiconductor composition includes a PTTP derivative, the organic semiconductor composition may also be somewhat susceptible to nonpolar organic solvents. Hence, organic dielectric compositions that are solvated by nonpolar organic solvents may at least slightly solvate PTTP derivative organic semiconductor compositions, thus negatively affecting charge carrier mobility. Accordingly, as an example, water-based organic dielectric compositions may be effectively used in combination with organic semiconductor compositions including PTTP derivatives.

Referring again to Formula 1, the $R^1$ and $R^2$ side chains may generate steric hindrance among the organic semiconductor molecules, reducing the tendency of the aromatic core regions of the organic semiconductor molecules to tightly pack together. This reduced packing may increase the solubility of the organic semiconductor in a given solvent. Such increased solubility may enable preparation of a solution containing an increased concentration of an organic semiconductor. Where a body of an organic semiconductor is to be deposited on a substrate, such a solution may enable deposition of a body of the organic semiconductor having an increased thickness. The steric hindrance generated by the alkyl side chains on the organic semiconductor molecules may also increase the flexibility of a resultant body of the organic semiconductor. Further, the alkyl side chains may be more flexible than are the relatively rigid core region structures including phenyl or thiophene rings or both. This increased flexibility may improve processability of the organic semiconductor composition during its fabrication into a body such as in a continuous printing process, and may increase durability of the resulting semiconductor composition body as incorporated in a device for an end-use application. Ether moieties in the side chains, if present, may further contribute to these effects on the performance of a device made utilizing the organic semiconductor.

The $R^1$ and $R^2$ groups contain some branching. Branching may generate steric hindrance between adjacent organic semiconductor molecules, further reducing the closeness of inter-molecular packing as compared with a semiconductor analog without the alkyl side chains. Branching may thus somewhat reduce charge carrier mobility of the semiconductor composition body, while the attendant steric hindrance may increase the solubility of the organic semiconductor composition in a suitable solvent.

The support body 405 may generally be formed from any material suitable for providing structural support directly to the organic semiconductor composition body 410 and indirectly to the dielectric composition body 420. The support body 405 may be rigid or flexible as needed for compatibility with the process for fabricating the laminate 400 and for compatibility with its intended end-use. In one example, the support body 405 is an elongated web formed of aluminum, a glass, or a polymer. Suitable polymers for this purpose include, for example, poly(ethylene terephthalate) generally referred to as PET (such as MYLAR® commercially available from E.I. du Pont de Nemours & Company or Melinex® available from Du Pont Teijin Films), polyethylene naphthalate ("PEN"), poly(ethylene terephthalate)-poly(ethylene naphthalate) copolymer ("PET/PEN"), and polyimides (such as Kapton® also commercially available from E.I. du Pont de Nemours & Company).

In one example, the dielectric composition may include any organic composition suitable to be formed into a solid body having adequate dielectric performance capability. Inorganic moieties, species, and elements may also be included in the organic dielectric composition. As examples, classes of suitable organic dielectric compositions include polyvinylpyrrolidone ("PVP"), polyvinylalcohol ("PVA"), and polyurethane ("PU"). The PVP, PVA and PU polymers may be doped, for example in the form of an aqueous dispersion, with an insulator such as $BaTiO_3$ in order to upwardly adjust the polymer's dielectric constant. $BaTiO_3$ is commercially available from Du Pont.

An example of a class of hydrophobic organic dielectric polymers that may be used is perfluoro(1-butenyl vinyl ether) homocyclopolymers. Such polymers are commercially available from the Asahi Glass Company under the trademark CYTOP® ("CYTOP"). In one example, a homopolymer having one of the following structures is employed:

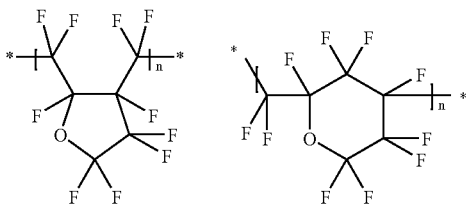

In another example, poly[4,5-difluoro-2,2-bis(trifluoromethyl)-1,3-dioxole-co-tetrafluoroethylene, having the following structure, may be utilized:

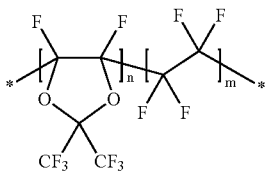

This fluorinated low k dielectric material is commercially available from Sigma-Aldrich under the trade name Teflon® AF 2400 (catalogue number 469629).

In an alternative example, an inorganic dielectric composition may be utilized. In the case of such a dielectric composition that may not be suitable for deposition by printing techniques, vapor deposition may be utilized. Such vapor deposition may involve deposition at high temperatures under a vacuum. Vapor deposition may not be compatible with some substrates, such as plastic support bodies.

In one example, the dielectric constant of the organic dielectric composition body is at least about two (2). In another example, the dielectric constant of the organic dielectric composition body is at least about four (4). In a further example, the dielectric constant of the organic dielectric composition body is within a range of between about six (6) and about forty (40).

Dielectric constant and volume resistivity data for examples of organic dielectric compositions are reported in Table 2. All dielectric constant data herein are unitless and were measured in accordance with IEC standard 60250. Volume resistivity was measured according to IEC 60093. Throughout this specification, reported dielectric constants and volume resistivities were determined for dielectric bodies standing alone. For each measurement of dielectric constant and volume resistivity, the organic dielectric composition was spin coated onto indium-tin oxide ("ITO")—coated glass and suitably dried to form a body. The ITO coating served as one electrode, and the other electrode was applied as a layer of conducting silver or carbon paint or colloidal graphite. The volume resistivity needs to be relatively high in order to insulate the gate electrode from the source and drain electrodes at the small dielectric body thicknesses employed.

TABLE 2

| Dielectric composition | Dielectric constant | volume resistivity (Ωcm) |
|---|---|---|
| PVA | 7.8*** | $8 \times 10^{12}$* $8 \times 10^{13}$** |
| PVP | 2.4**** | $3 \times 10^{13}$* $4 \times 10^{11}$** |
| PVP/BaTiO$_3$ dispersion | 26.5**** | $1 \times 10^{11}$* $1 \times 10^{13}$** |
| Cytop ® Perfluoro(1-butenyl vinyl ether) homo cyclopolymer | 2.1*** | $3 \times 10^{15}$* $6 \times 10^{14}$** |

TABLE 2-continued

| Dielectric composition | Dielectric constant | volume resistivity (Ωcm) |
|---|---|---|
| PU | 6*** | $1 \times 10^{13}$-$1 \times 10^{14}$*** |
| Luxprint ® polymer | 40*** | |

Figure 5:
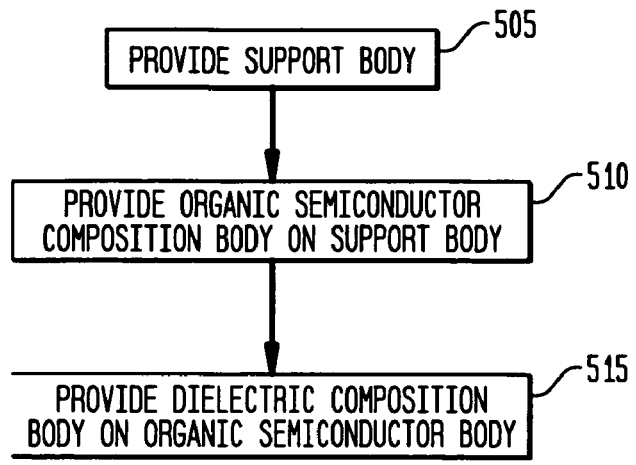
FIG. 5 shows an example of a process for fabrication of the laminate shown in FIG. 4.

*after 10 minutes drying at 80° C.
**after 10 minutes drying at 80° C. and then 5 minutes at room temperature in air
***at room temperature in air
****at 25° C., 50% relative humidity FIG. 5 shows an example of an implementation of a process 500 for fabrication of the laminate 400. In step 505, a support body 405 is provided as earlier discussed. In step 510, an organic semiconductor composition body 410 is provided on the support body 405. The organic semiconductor body 410 may be formed in any suitable manner on the support body 405. For example, a selected organic semiconductor composition may be vaporized and deposited onto the support body 405. Alternatively for example, a selected organic semiconductor may be mobilized in a liquid medium and deposited onto the support body 405. The liquid medium may be removed, for example, by directing an inert gas such as nitrogen over the laminate 400. Heat may also be applied.

In step 515, a dielectric composition body 420 is provided on the organic semiconductor body 410. The dielectric body 420 may be formed in any suitable manner on the organic semiconductor body 410. For example, a selected dielectric composition may be vaporized and deposited onto the organic semiconductor body 410. Alternatively for example, a selected dielectric composition may be mobilized in a liquid medium and deposited onto the organic semiconductor body 410. In one example, a spin-casting process may be employed to apply the dielectric composition in order to form the dielectric composition body 420. The liquid medium may be removed, for example, by directing an inert gas such as nitrogen over the laminate 400. Heat may also be applied.

FIG. 6 shows a cross-sectional side view of an example of a laminate 600 having a support body 605 having bonded thereon an organic semiconductor composition body 610. Interposed between regions 604, 606 and 608 of the organic semiconductor composition body 610 on the support body 605 are source and drain electrodes 603 and 607, respectively. The organic semiconductor composition body 610 forms an interface 615 with a dielectric composition body 620 bonded to the organic semiconductor composition body 610. In this example, the source and drain electrodes 603 and 607 penetrate partially into the dielectric composition body 620, as indicated by ticked lines. In an alternative example, the source and drain electrodes 603 and 607 do not penetrate into the dielectric composition body 620. The organic semiconductor composition body 610 is interposed between the support body 605 and the dielectric composition body 620. A gate electrode 625 is bonded onto the dielectric composition body 620. The laminate 600 may for example be fabricated by first providing the source and drain electrodes 603 and 607, respectively, on the support body 605. The source and drain may be made using various techniques such as laser ablation and offset printing. The organic semiconductor composition body 610 is then provided on the support body 605. Next, the dielectric composition body 620 is provided to form the interface 615 with the organic semiconductor composition body 610. The gate electrode 625 is then provided on the dielectric composition body 620.

The source and drain electrodes 603 and 607 respectively may be fabricated directly onto the support body 605. Referring to FIG. 6, the source electrode 603 and drain electrode 607 are laterally defined and mutually spaced apart along the interface 601 between the support body 605 and the organic semiconductor composition body 610, in order to avoid electrical shorting. Hence, this direct fabrication permits optimization of deposition conditions for the source electrode 603 and the drain electrode 607. Fabrication of the organic semiconductor composition body 610 prior to fabrication of the dielectric composition body 620 enables the realization of this direct fabrication of the source electrode 603 and the drain electrode 607 on the support body 605.

In this example, the organic semiconductor composition body 610 may be fabricated on the support body 605 from either a liquid or vapor phase, as the composition of the support body 605 may readily be selected from a broad range of potential materials that are not adversely affected by, nor that adversely affect, the organic semiconductor composition body 610 being formed. In one example, the dielectric composition body 620 may be fabricated from a dielectric composition mobilized in a liquid medium.

The example of a laminate 600 may be operated as an FET, by connecting the source and drain electrodes 603 and 607 and the gate electrode 625 to external circuitry. In one example, access to the source electrode 603 and the drain electrode 607 for such external connections is provided by pathways made through the dielectric composition body 620. In another example, the support body 605 is completely or partially removed to facilitate external connections.

Figure 7:
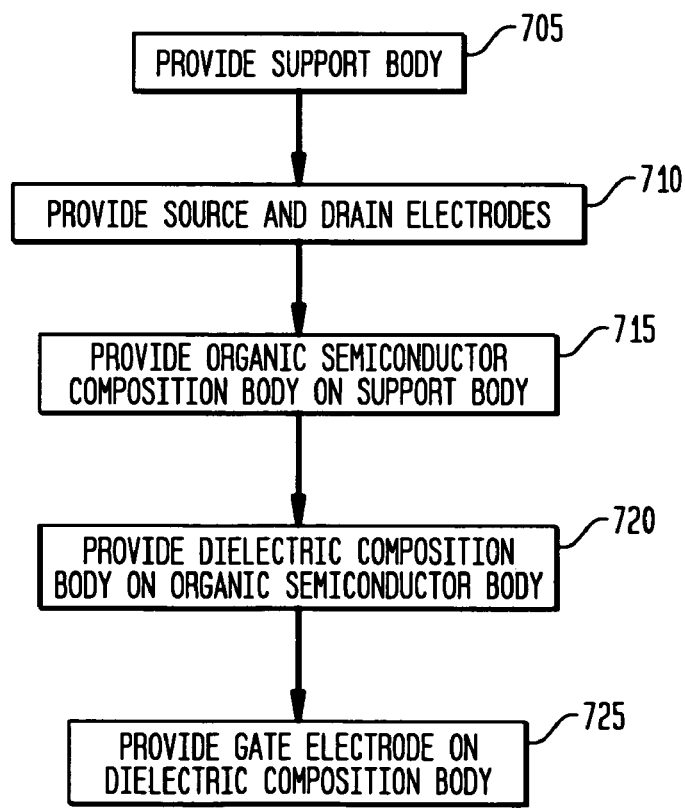
FIG. 7 shows an example of a process for fabrication of the laminate shown in FIG. 6.

FIG. 7 shows an example of an implementation of a process 700 for fabrication of the laminate 600. In step 705, a support body 605 is provided as earlier discussed. In step 710, source and drain electrodes 603 and 607, respectively, are provided on the support body 605. The source electrode 603 and drain electrode 607 may be formed in any suitable manner on the support body 605. For example, a selected charge carrier conductive composition such as a metal or metal alloy including copper, aluminum, gold, silver, platinum, palladium, and/ or nickel, may be electroplated or vaporized and deposited through a mask onto the support body 605. Alternatively, a conductive body formed from a selected charge carrier conductive composition may be deposited by any suitable process onto the support body 605, such as by electrodeposition, direct coating, or sputtering, and then selectively etched. Further, a selected charge carrier conductive polymer such as polyethylenethioxythiophene ("PEDOT"), may be mobilized by a suitable solvent and printed onto the support body 605. In step 715, an organic semiconductor composition body 610 is provided on the support body 605. The organic semiconductor composition body 610 may be formed in any suitable manner on the support body 605, as discussed in connection with FIG. 6. In step 720, a dielectric composition body is provided on the organic semiconductor composition body 610. In one example, a spin-casting process may be employed to apply the dielectric composition in a form mobilized in a liquid medium in order to form the dielectric composition body 620. The liquid medium may then be removed, for example, by directing an inert gas such as nitrogen over the laminate 600. Heat may also be applied.

In step 725, the gate electrode 625 is provided on the dielectric composition body 620. The gate electrode 625 may be formed in any suitable manner on the dielectric composition body 620. For example, a selected charge carrier conductive composition as discussed earlier may be vaporized or solvated and deposited onto the dielectric composition body 620. Vaporization, if employed, is carried out with care to minimize disturbance of the organic semiconductor and dielectric compositions. The selected charge carrier conductive composition may be deposited by any other suitable process onto the dielectric composition body 620. Masking and etching processes or printing processes may be carried out if desired, for example if multiple laminates 600 are being simultaneously fabricated on an integral support body 605.

FIG. 8 shows a cross-sectional side view of an example of a laminate 800 having a support body 805 having bonded thereon a dielectric composition body 810. The dielectric composition body 810 forms an interface 815 with an organic semiconductor composition body 820 bonded to the body 810. The dielectric composition body 810 is interposed between the support body 805 and the organic semiconductor composition body 820. The laminate 800 may for example be fabricated by first providing the dielectric composition body 810 on the support body 805, and then providing the organic semiconductor composition body 820 to form the interface 815 with the dielectric composition body 810.

Figure 9:
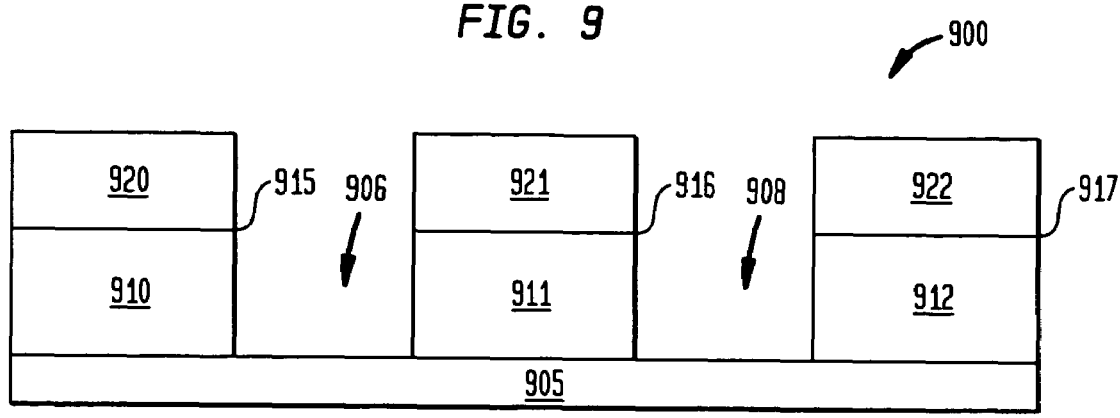
FIG. 9 shows a cross-sectional side view of an example of a laminate including a support body having bonded thereon a plurality of organic semiconductor composition bodies and a plurality of dielectric composition bodies over intermittent regions of the support body.

FIG. 9 shows a cross-sectional side view of an example of a laminate 900 having a support body 905 having bonded thereon a plurality of organic semiconductor composition bodies 910, 911 and 912 over intermittent regions of the support body 905. A plurality of examples of exposed regions 906 and 908 of the support body 905 serve to mutually space apart the organic semiconductor composition bodies 910-912. The organic semiconductor composition bodies 910, 911 and 912 respectively form interfaces 915, 916 and 917 with dielectric composition bodies 920, 921 and 922 respectively bonded to the semiconductor composition bodies 910, 911 and 912. The organic semiconductor composition bodies 910-912 are interposed between the support body 905 and the dielectric composition bodies 920-922, respectively. The laminate 900 may for example be fabricated by first providing the organic semiconductor composition bodies 910-912 on the support body 905, and then providing the dielectric composition bodies 920-922 in registration with the organic semiconductor composition bodies 910-912 to form the interfaces 915-917, respectively. In this regard, the support body 905 as shown in FIG. 9 may be a representative portion of an elongated web on which the laminate 900 may be fabricated on a continuous basis in any desired length.

In one example, the process 500 may be carried out on an elongated web in order to produce a plurality of laminates 900. The elongated web may, for example, be suitable for reel-to-reel continuous processing of a high surface area having a plurality of laminates 900 in a spaced apart array on the elongated web. In one example, the laminates 900 may have examples of exposed regions 906 and 908. In this case, the organic semiconductor composition may be intermittently applied onto the support body 905 to form the representative organic semiconductor composition bodies 910-912. The dielectric composition may then be applied onto the organic semiconductor composition bodies 910-912, and if desired, may also be applied over the representative exposed regions 906 and 908 of the support body 905 to form an elongated body of the dielectric composition. Alternatively, the organic semiconductor composition bodies 910-912 may be integrated into an elongated organic semiconductor composition body on the support body 905, and the dielectric composition bodies 920-922 may be integrated into an elongated dielectric composition body on the support body 905. In the latter case an elongated three-body laminate is formed having the structure of the laminate 400 shown in FIG. 4. Referring to FIGS. 6 and 8, the laminate 600 and laminate 800 may analogously constitute elongated multi-body laminates.

In one example, the process 500 may be carried out on an elongated web in order to produce a plurality of laminates 900 using a continuous gravure printing process. Gravure, a type of intaglio printing, makes use of the ability of ink to adhere to shallow scratches and depressions on a polished metal plate. In one example, rotogravure is used, employing a web press equipped with a cylindrical metal plate that rotates on its axis. A web or sheet of a selected elongated support body passes between the rotating cylindrical plate and an impression roll, transferring ink onto the elongated support body. Gravure inks generally have a low viscosity in order to allow them to be drawn into engraved cells on the metal gravure plate and then be transferred onto the elongated support body. High volume air dryers are placed in position to then dry the ink prior to any subsequent additional printing steps. Water-based inks require a higher drying temperature and longer drying time than do inks employing more volatile solvents having a higher vapor pressure.

In another example, the process 500 is carried out on an elongated web in order to produce a plurality of laminates 900, using a continuous offset printing process. For example, offset gravure or offset lithography may be used. In offset printing processes, ink is not applied directly from a printing plate or cylinder to the elongated support body. Instead, ink is applied to the printing plate to form the image to be printed, and is then transferred to a rubber blanket. The image on the blanket is then transferred to the elongated support body. In lithography, the intended image areas of the printing plate or cylinder are treated to make them selectively hydrophobic, and the remaining surface area of the plate or cylinder remains hydrophilic. An aqueous fountain solution is then applied to the plate or cylinder to wet the hydrophilic regions and prevent subsequent adherence of a hydrophobic ink to them. A hydrophobic ink composition is then applied to the image areas of the plate or cylinder. The image is then successively transferred to the offset blanket and then to the elongated support body. Printing inks for offset lithography generally are viscous and paste-like, in order to reduce their flow beyond the image areas onto the non-image hydrophobic areas.

Other printing processes may be used. For example, ink jet printing may be used. However, ink jet printing is generally imprecise and implicates transfer of ink particles across a distance onto the body, which typically is not optimum for a continuous fabrication process.

The organic semiconductor composition bodies and the dielectric composition bodies may be fabricated on the support body in each case using a printing ink including the respective compositions. The solvents employed in making such inks are desirably selected to have boiling points that are not too low or too high. In one example, the solvents have boiling points within a range of between about 50° C. and about 200° C. In another example, the solvents have boiling points within a range of between about 60° C. and about 150° C. If the solvent boiling point is too high, then evaporation of the solvent after printing of the ink may become problematic. If the solvent boiling point is too low, then the composition may also be tacky at moderate temperatures such that its physical structure remains unstable. The surface tension of the printing ink needs to be sufficiently low so that the ink may wet the support body surface and be separated from the support body surface, and if employed, the offset blanket. In one example of gravure printing, an ink is used having a surface tension within a range of between about 22 milli-newtons per meter ("mN/m") and about 32 mN/m; and having a viscosity within a range of between about 40 milli-Pascals per second ("mPas") and about 800 mPas. In one example of offset printing, an ink is used having a surface tension within a range of between about 30 mN/m and about 60 mN/m; and having a viscosity within a range of between about 5000 mPas and about 100,000 mPas.

EXAMPLE 1

FETs were fabricated using some of the organic semiconductors defined in Table 1. The FET structures fabricated included silicon wafers having overlaid silicon dioxide bodies, onto which the various PTTP semiconductors in Table 1 were deposited, followed by addition of gold source and drain electrodes. The silicon and silicon dioxide served as gate electrode and gate dielectric, respectively. The various PTTP semiconductors were either sublimed onto the silicon dioxide body on the wafer, or drop cast from solution. In one example, an FET was made having an organic semiconductor composition body 410 including 6-O-PTTP-O-6: $\mu=1-1.5\times10^{-3}$ cm$^2$/Vs (fabrication of gate electrode/dielectric body/semiconductor body/source-drain electrodes: drop casting, Si/SiO$_2$/PTTP composition/Au). In a further example, an FET was made having an organic semiconductor composition body 410 including 5(4Me)-O-PTTP-O-5(4(Me): $\mu=1-3\times10^{-4}$ cm$^2$/Vs(drop casting, Si/SiO$_2$/PTTP composition/Au); $\mu=(1.7-4.0)\times10^{-3}$ cm$^2$/Vs (sublimed films at room temperature, Si/SiO$_2$/PTTP composition/Au); $\mu=(6.1-8.5)\times10^{-3}$ cm$^2$/Vs (sublimed films at 70° C., Si/SiO$_2$/PTTP composition/Au). In an additional example, an FET was made having an organic semiconductor composition body 410 including 8(3,7Me)-O-PTTP-O-8(3,7Me): $\mu=6\times10^{-6}$-5$\times10^{-5}$ cm$^2$/Vs (drop casting, Si/SiO$_2$/PTTP composition/Au). In another example, an FET was made having an organic semiconductor composition body 410 including 4(2Et)-O-PTTP-O-4(2Et): $\mu=10^{-6}$-5$\times10^{-5}$cm$^2$/Vs (drop casting, Si/SiO$_2$/PTTP composition/Au). In a further example, an FET was made having an organic semiconductor composition body 410 including 6(2Me)-O-PTTP-O-6(2Me): $\mu=(2.0-2.7)\times10^{-4}$ cm$^2$/Vs (sublimed films at room temperature, Si/SiO$_2$/PTTP composition/Au); $\mu=(3.3-4.8)\times10^{-4}$ cm$^2$/Vs (sublimed films at 70° C., Si/SiO$_2$/PTTP composition/Au). In an additional example, an FET was made having an organic semiconductor composition body 410 including 6(2Et)-O-PTTP-0-6(2Et): $\mu=5\times10^{-8}$-7$\times10^{-7}$ cm$^2$/Vs (drop casting, Si/SiO$_2$/PTTP composition/Au); $\mu=(1.2-2.4)\times10^{-5}$ cm$^2$/Vs (sublimed films at room temperature, Si/SiO$_2$/ PTTP composition/Au); $\mu=(6.2-9.4)\times10^{-5}$ cm$^2$/Vs (sublimed films at 70° C., Si/SiO$_2$/ PTTP composition/Au). In another example, an FET was made having an organic semiconductor composition body 410 including 6(1Me)-O-PTTP-O-6(1Me): $\mu=(1.2-4.3)\times10^{-4}$ cm$^2$/Vs (sublimed films at room temperature, Si/SiO$_2$/PTTP composition/Au); $\mu=(6.5-9.8)\times10^{-4}$ cm$^2$/Vs (sublimed films at 70° C., Si/SiO$_2$/PTTP composition/Au). In a further example, an FET was made having an organic semiconductor composition body 410 including 6(1Et)-O-PTTP-O-6(1Et): $\mu=(3.1-3.3)\times10^{-7}$ cm$^2$/Vs (sublimed films at temperature, Si/SiO$_2$/PTTP composition/Au); $\mu=4.4\times10^{-7}$ cm$^2$/Vs (sublimed films at 70° C., Si/SiO$_2$/PTTP composition/Au). Additional trials utilizing 302PTTP02 and following the same procedure yielded FETs having mobilities within a range of between about $1\times10^{-4}$ cm$^2$/Vs and $3\times10^{-3}$ cm$^2$/Vs.

EXAMPLE 2

A study was carried out to compare the charge carrier mobility of an FET prepared utilizing 6(1Me)-O-PTTP-O-6(1Me), also referred to in this specification as 1-MH-PTTP, with the charge carrier mobility of an FET prepared utilizing 7(2Me)-PTTP-7(2Me). The structural formulas for these semiconductor compositions are shown in Table 2 below. It can be seen that the structure of 7(2Me)-PTTP-7(2Me) is similar to that of 6(1Me)-O-PTTP-O-6(1 Me). However, 7(2Me)-PTTP-7(2Me) does not include ether moieties in the alkyl side chains. Accordingly, 7(2Me)-PTTP-7(2Me) may serve as indicative of the impact of exclusion or inclusion of the ether moieties in 6(1Me)-O-PTTP-O-6(1 Me) on the charge carrier mobility of an FET incorporating the latter semiconductor composition.

Before fabricating the FETs, the solubility of the two semiconductor compositions in tetrahydrofuran (THF) was determined. The 6(1Me)-O-PTTP-O-6(1Me), having ether moieties, had approximately twice the solubility in THF as did 7(2Me)-PTTP-7(2Me). Table 2 shows that the solubility of 6(1Me)-O-PTTP-O-6(1Me) in THF was 89,000ppm, or 8.9%. Table 2 further shows that the solubility of 7(2Me)-PTTP-7(2Me) in THF was only 45,000ppm, or 4.5%. Hence 6(1Me)-O-PTTP-O-6(1 Me), within the scope of Formula 1, demonstrated greater solubility, which may indicate better processability by preparing a semiconductor composition body from solution in the fabrication of, as an example, an FET.

FETs were then fabricated, including silicon wafers having overlaid silicon dioxide bodies, onto each of the two semiconductors in Table 2 were separately deposited, followed by addition of gold source and drain electrodes. The silicon and silicon dioxide served as gate electrode and gate dielectric, respectively. The semiconductors were sublimed at 70° C. onto the silicon dioxide body on the wafer. In the case of an FET having the structure discussed in connection with FIG. 4 with an organic semiconductor composition body 410 including 6(1Me)-O-PTTP-O-6(1 Me), the mobility $\mu=1\times10^{-3}$ cm$^2$/Vs. In the case of an FET having the structure discussed in connection with FIG. 4 with an organic semiconductor composition body 410 including 7(2Me)-PTTP-7(2Me), the mobility $\mu=4\times10^{-4}$ cm$^2$/Vs. Hence, the semiconductor composition including alkyl side chains having ether moieties yielded an FET having a relatively higher charge carrier mobility.

TABLE 2

| 6(1Me)-O-PTTP-O-6(1Me) | 5,5'-bis(4-(1-methylhexyloxy)phenyl)-2,2'-bithiophene 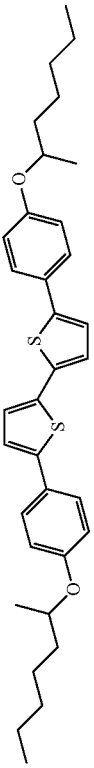 Molecular Weight = 546.84 Exact Mass = 546 Molecular Formula = C34H42O2S2 Molecular Composition = C 74.68% H 7.74% O 5.85% S 11.73% | S: route D, FIG. 2 P: filtration (SiO₂), extraction Y: 19 S: route B, FIG. 2 P: extraction Y: 52, 36, 51, and 44% S: route B, FIG. 2 P: 2 × precipitation from toluene with methanol Y: 39% | well soluble in THF (about 89,000); o-xylene 54,000 ppm; THF/cyclohexanol 2:8 (viscosity 9 mPas) 4,000 ppm 2-Ethylhexanol: about 800 ppm DSC: mp = 143° C., smaller transition at 118° C., 129° C. and 132° C. |
|---|---|---|---|
| 7(2Me)-PTTP-7(2Me) | 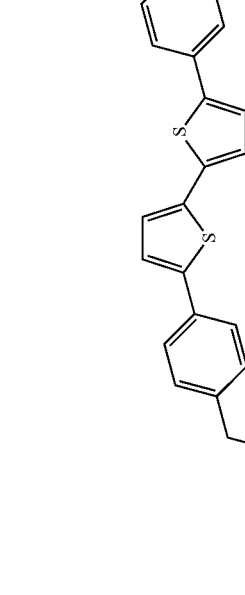 Molecular Weight = 542.90 Exact Mass = 542 Molecular Formula = C36H46S2 Molecular Composition = C 79.65% H 8.54% S 11.81% 5,5'-bis(4-(2-methylheptyl)phenyl)-2,2'-bithiophene | S: FIG. 3 P: extraction Y: 54% | well soluble in THF, but not better than oxygen-containing analogue "6(1Me)-O" (about 45,000 ppm) |

EXAMPLE 3

An FET having a structure consistent with that shown in FIG. 6 was fabricated using the process described in connection with FIG. 7. The support body used was a polyethylene naphthalate ("PEN") polyester foil obtained from DuPont Teijin Films U.S. Limited Partnership, 1 Discovery Drive, P.O. Box 411, Hopewell, Va. 23860 U.S.A., sold under the trade name, Teonex Q 51, attached to a glass slide with scotch tape. The source and drain electrodes were fabricated from polyethylenedioxythiophene ("PEDOT"), offset printed at an average thickness of about 1 micron ("μ"). The channel length, the minimum path distance between the source and drain electrodes, ("L") was 120 microns. The organic semiconductor composition body used was spin coated from a 5% weight/weight solution in tetrahydrofuran (THF) of 5,5'-bis (4-(1-methylhexyloxy)phenyl)-2,2'-bithiophene ("1-MH-PTTP"), and had an average thickness of about 200 nanometers ("nm"). The organic dielectric composition body was spin coated from an aqueous solution of polyvinyl alcohol ("PVA"), having an average thickness of about 1.4 μ. The gate electrode was gold evaporated onto the organic dielectric composition body. The resulting FET was connected into an external circuit. The mobility of the FET was $1 \times 10^{-3}$ centimeters squared per volt-second ("cm$^2$/Vs"), and the on/off ratio was 190 calculated from the output characteristic.

An additional FET was fabricated in the same manner as reported above in this Example 3, except that: the source and drain electrodes were fabricated of gold, formed by evaporation; the organic semiconductor composition body used was spin coated from a 3% weight/weight solution in THF; and the organic dielectric composition body was spin coated from an aqueous solution of PVA, having an average thickness of about 3.5 μ. In addition, after spin coating, the semiconductor composition body was annealed at 150° C. for 15 minutes and then slowly cooled, which may yield more and better semiconductor crystal domains. The melting point of 1-MH-PTTP is 145° C., slightly below the annealing temperature. The mobility of the FET was $4.8 \times 10^{-3}$ cm$^2$/Vs, and the on/off ratio was 6 calculated from the output characteristic.

EXAMPLE 4

An additional FET was fabricated in the same manner, except that the source and drain electrodes were laser-patterned and a 0.5% weight/weight solution in tetrahydrofuran (THF) of 1-MH-PTTP was used, further including 1% by weight of polystyrene ("PS") having an average molecular weight of about $2.75 \times 10^6$ grams per mole and a polydispersivity ("PDI") of about 1.05. The apparent viscosity η of a 10% weight/weight solution of PS in THF is 400 milliPascal seconds ("mPas") at a shear rate γ of 100/second ("s"). Accordingly, PS may be used to adjust the rheological properties of the semiconductor printing ink, such as viscosity, surface tension and adhesion. The PS-modified organic semiconductor composition was used to fabricate an organic semiconductor composition body having an average thickness of about 1,700 nm. The organic dielectric composition body was spin coated from an aqueous solution of PVA, having an average thickness of about 3,500 nm. The mobility of the FET was $7 \times 10^{-3}$ cm$^2$/Vs, and the on/off ratio, calculated from the output characteristics, was 20. Hence, addition of the PS to improve printability of the organic semiconductor ink did not adversely affect the mobility of the fabricated FET. Further information on fabrication of active devices utilizing organic semiconductor compositions including polystyrene additives is disclosed in U.S. patent application Ser. No. 11/240,733, filed concurrently herewith by Florian Dötz, Ingolf Hennig and Frauke Richter and owned by BASF Aktiengesellschaft, entitled "ORGANIC COMPOSITIONS", the entirety of which hereby is incorporated herein by reference.

EXAMPLE 5

Figure 10:
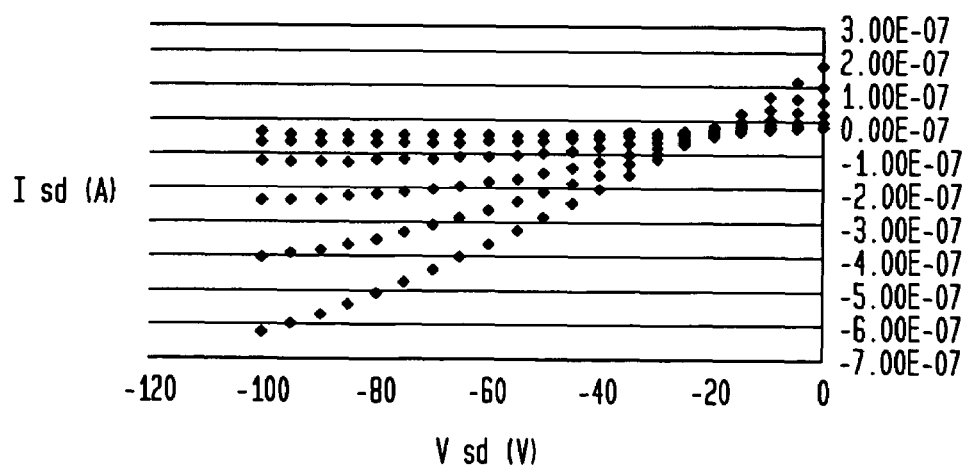
FIG. 10 shows graphs plotting the drain-source current versus the drain-source voltage for Example 5, using various applied gate voltages.

An FET having a structure consistent with that shown in FIG. 6 was fabricated using the process described in connection with FIG. 7. The support body used was a PEN foil attached to a glass slide. The source and drain electrodes were fabricated from gold, vapor evaporated at an average thickness of 0.1 μ. The organic semiconductor composition body used was vapor deposited 5,5'-bis(4-propoxyethyl)-2,2'-bithiophene ("3O2PTTP2O3"), and had an average thickness within a range of between about 50 nm and about 250 nm. An organic dielectric composition body was dip coated at a rate of 0.5 centimeters per second onto the organic semiconductor composition body from a 15% weight/weight aqueous solution of PVA, having an average thickness of about 2 μ. The gate electrode was conductive carbon paint applied onto the PVA dielectric composition body. The resulting FET was connected into an external circuit. The mobility of the FET was $3 \times 10^{-3}$ cm$^2$/Vs, and the on/off ratio was 27.1. FIG. 10 shows a graph plotting the drain-source current (Isd(A)) versus the drain-source voltage (Vsd(V)). In the graph, the scale on the right is exponential; "3.00E-07" signifies $3 \times 10^{-7}$.

For an example of a p-type semiconductor capable of transporting holes, electrical conductivity is approximated by the formula a $\sigma = en\mu_d$ where $\mu^d$ is the carrier mobility, e is the charge on the carriers, and n is the density of free carriers. Conductivity accordingly is proportional to mobility. Mobility may readily be measured, and the corresponding conductivity may be approximated. Conductivity in a device having an organic semiconductor depends on the size and separation of crystal grains. The size distribution of crystal grains determines how many of them must be effectively traversed by a charge carrier in order to be transported from an origin to a destination such as between a source and a drain, for example. The separation between crystal grains determines the impact of non-crystalline regions on conductivity. For example, crystal grains separated by a distance greater than the maximum inter-grain tunneling distance for a particular semiconductor material may constitute a nonconductive pathway for charge carriers. Conductivity within a crystal grain of an organic semiconductor also depends on charge carrier energy levels and molecular overlaps in the crystal.

Since conductivity is proportional to mobility for materials with one charge carrier type, and mobility may be directly measured, the mobility is generally considered to be the most important parameter for characterization of transistors such as FETs. The On/Off ratio is generally considered to be the second most important parameter. The measurements of the FETs fabricated as reported above were performed with a Hewlett-Packard 4155 A Semiconductor Parameter Analyzer in Examples 1, 2 and 5; and an Agilent E5273A source meter in Examples 3-4.

The following formula was used to determine the mobility, in saturation regime, of the transistors fabricated in accordance with Examples 1, 2 and 5.

$$I_{ds} = W/2L \times C_i \mu (Vg - Vt)^2 \tag{2}$$

In formula (2), $I_{ds}$ is the saturation drain-source current, W is the width of the source-drain gap, L is the length of the gap, $C_i$ is the capacitance of the organic dielectric composition body, μ is the mobility in cm$^2$/Vs, $V_g$ is the gate electrode voltage and $V_t$ is the threshold voltage. An applied drain-source current within a range of between −100 volts and 0 volts at intervals of −20 volts was used in testing the transistors. The capacitance of the organic dielectric composition bodies in the FETs was directly measured by probes attached to a Hewlett-Packard inductance-capacitance-resistance meter with an applied current. The W/L ratio was measured by using an optical microscope.

The following formula was used to determine the mobility, in linear regime, of the transistors fabricated in accordance with Examples 3-4. This methodology may yield mobilities having a magnitude about twice as large as the methodology discussed above in connection with Examples 1, 2 and 5.

$$\mu = (\partial I_{ds}/\partial Vg) \cdot (L/WciV_{ds}) \quad (3)$$

In formula (3), $I_{ds}$ is the drain-source (or source-drain) current in the linear regime (IVdI <IVgI). Vg is the gate electrode voltage, $V_{ds}$ is the drain-source (or source-drain) voltage, $C_i$ is the gate insulator capacitance per unit area, L is the channel length, W is the channel width, and $\partial$ denotes a partial derivative. The voltages for the measurement of the output characteristics were varied in the following range: $0V \geq Vds \geq -60V$ (10 V steps), $10 V \geq Vgs \geq -60 V$ (10 V steps). The gate insulator capacitance in the FETs was directly measured by probes attached to the Hewlett-Packard inductance-capacitance-resistance meter. The W/L ratio was measured using an optical microscope.

While the present invention has been disclosed in a presently preferred context, it will be recognized that the present teachings may be adapted to a variety of contexts consistent with this disclosure and the claims that follow. For example, although specific examples have been discussed with respect to FETs, other active electronic devices may be fabricated.

We claim:
1. A molecule having the following formula:

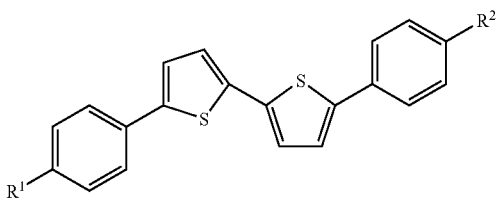

wherein each of $R^1$ and $R^2$ includes a branched alkyl group having 5 to 20 carbon atoms and an ether moiety; wherein each of $R^1$ and $R^2$ is linked by the ether moiety to one of the benzene rings; and wherein the molecule is a member selected from a group consisting of:
5,5'-bis(4-(4-methylpentyloxy)phenyl)-2,2'-bithiophene;
5,5'-bis(4-(3,7-dimethyloctyloxy)phenyl)-2,2'-bithiophene;
5,5'-bis(4-(3S,7-dimethyloctyloxy)phenyl)-2,2'-bithiophene;
5,5'-bis(4-(2-ethylbutyloxy)phenyl)-2,2'-bithiophene;
5,5'-bis(4-(2-methylhexyloxy)phenyl)-2,2'-bithiophene;
5,5'-bis(4-(2-ethylhexyloxy)phenyl)-2,2'-bithiophene;
5,5'-bis(4-(1-methylhexyloxy)phenyl)-2,2'-bithiophene;
5,5'-Bis-[4-(1-ethyl-hexyloxy)-phenyl]-[2,2']bithiophenyl;
5,5'-Bis-[4-(2-methyl-propoxy-tetrahydro-pyran)-phenoxy]-[2,2']bithiophenyl;
3-(4-{5'-[4-(3-Hydroxy-2-methyl-propoxy)-phenyl]-[2,2']bithiophenyl-5-yl}-phenoxy) -2-methyl-propan-1-ol;
6-[4-(5'-{4-[5-(1-Vinyl-allyloxycarbonyl)-pentyloxy]-phenyl}-[2,2']bithiophenyl-5-yl)-phenoxy]-hexanoic acid 1-vinyl-allyl ester; and
5,5'-Bis-{4-[6-(tert-butyl-diphenyl-silanyloxy)-hexyloxy]-phenyl}-[2,2']bithiophenyl.

2. The molecule of claim 1, wherein the molecule is 5,5'-bis(4-(1-methylhexyloxy)phenyl)-2,2'-bithiophene.

3. The molecule of claim 1, wherein the molecule is 5,5'-bis(4-(2-methylhexyloxy)phenyl)-2,2'-bithiophene.

4. The molecule of claim 1, wherein the molecule is 5,5'-bis(4-(4-methylpentyloxy)phenyl)-2,2'-bithiophene.

5. The molecule of claim 1, wherein the molecule is 5,5'-bis(4-(3,7-dimethyloctyloxy)phenyl)-2,2'-bithiophene.

6. The molecule of claim 1, wherein the molecule is 5,5'-bis(4-(3S,7-dimethyloctyloxy)phenyl)-2,2'-bithiophene.

7. The molecule of claim 1, wherein the molecule is 5,5'-bis(4-(2-ethylbutyloxy)phenyl)-2,2'-bithiophene.

8. The molecule of claim 1, wherein the molecule is 5,5'-bis(4-(2-ethylhexyloxy)phenyl)-2,2'-bithiophene.

9. The molecule of claim 1, wherein he molecule is 5,5'-Bis-[4-(1-ethyl-hexyloxy)-phenyl]-[2,2']bithiophenyl.

10. The molecule of claim 1 wherein the molecule is 5,5'-Bis-8 4-(2-methyl-propoxy-tetrahydro-pyran)-phenoxy]-[2,2']bithiophenyl.

11. The molecule of claim 1, wherein the molecule is 3-(4-{5'-[4-(3-Hydroxy-2-methyl-propoxy)-phenyl]-[2,2']bithiophenyl-5-yl}-phenoxy) -2-methyl-propan-1-ol.

12. The molecule of claim 1, wherein the molecule is 6-[4-(5'-{4-[5-(1-Vinyl-allyloxycarbonyl)-pentyloxy]-phenyl}-[2,2']bithiophenyl -5-yl) -phenoxy]-hexanoic acid 1-vinyl-allyl ester.

13. The molecule of claim 1, wherein the molecule is 5,5'-Bis-{4-[6-(tert-butyl -diphenyl-silanyloxy)-hexyloxy]-phenyl}-[2,2']bithiophenyl.

14. A molecule having the following formula:

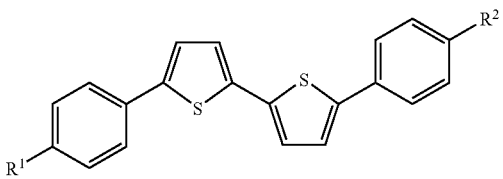

wherein each of $R^1$ and $R^2$ includes a branched alkyl group having 5 to 20 carbon atoms; and wherein the molecule is a member selected from a group consisting of:
5,5'-bis(4-(2-methylheptyl)phenyl)-2,2'-bithiophene;
5,5'-bis(4-(1-methylhexyl)phenyl)-2,2'-bithiophene;
5,5'-Bis-[4-(1-hydroxy-3-ethyl-heptyloxy)-phenyl]-[2,2'] bithiophenyl;
5,5'-Bis-[4-N-(2-ethyl-hexyl)-benzamido]-[2,2'] bithiophenyl; and
5,5'-bis(4-(propoxy ethyl)phenyl)-2,2'-bithiophene.

15. The molecule of claim 14, wherein the molecule is 5,5'-bis(4-(2-methylheptyl)phenyl)-2,2'-bithiophene.

16. The molecule of claim 14, wherein the molecule is 5,5'-bis(4-(1-methylhexyl)phenyl)-2,2'-bithiophene.

17. The molecule of claim 14, wherein the molecule is 5,5'-Bis-[4-(1-hydroxy -3-ethyl-heptyloxy)-phenyl]-[2,2']bithiophenyl.

18. The molecule of claim 14, wherein the molecule is 5,5'-Bis-[4-N-(2-ethyl -hexyl)-benzamido]-[2,2']bithiophenyl.

19. The molecule of claim 14, wherein the molecule is 5,5'-bis(4-(propoxy ethyl)phenyl)-2,2'-bithiophene.

* * * * *